US009243230B2

(12) United States Patent
Charleston et al.

(10) Patent No.: US 9,243,230 B2
(45) Date of Patent: Jan. 26, 2016

(54) CONSTRUCT FOR PRODUCING EMPTY VIRUS CAPSIDS

(75) Inventors: Bryan Charleston, Pirbright (GB); Ian Jones, Pirbright (GB)

(73) Assignee: THE PIRBRIGHT INSTITUTE, Pirbright, Woking (GB)

( * ) Notice: Subject to any disclaimer, the term of this patent is extended or adjusted under 35 U.S.C. 154(b) by 0 days.

(21) Appl. No.: 13/502,014

(22) PCT Filed: Sep. 24, 2010

(86) PCT No.: PCT/GB2010/001807
§ 371 (c)(1),
(2), (4) Date: Jun. 13, 2012

(87) PCT Pub. No.: WO2011/048353
PCT Pub. Date: Apr. 28, 2011

(65) Prior Publication Data
US 2012/0258133 A1    Oct. 11, 2012

(30) Foreign Application Priority Data

Oct. 20, 2009  (GB) .................................. 0918375.7

(51) Int. Cl.
| | |
|---|---|
| *C07H 21/04* | (2006.01) |
| *C12Q 1/68* | (2006.01) |
| *C07K 14/435* | (2006.01) |
| *C12N 15/85* | (2006.01) |
| *C12N 15/86* | (2006.01) |
| *C12N 7/00* | (2006.01) |
| *C07K 14/005* | (2006.01) |
| *C07K 14/47* | (2006.01) |

(52) U.S. Cl.
CPC ............... *C12N 7/00* (2013.01); *C07K 14/005* (2013.01); *C07K 14/4747* (2013.01); *C12N 2770/32122* (2013.01); *C12N 2770/32123* (2013.01); *C12Q 1/6886* (2013.01); *C12Q 2600/136* (2013.01); *C12Q 2600/156* (2013.01); *G01N 2333/4704* (2013.01)

(58) Field of Classification Search
CPC ............. C07K 14/4747; C12Q 1/6886; C12Q 2600/136; C12Q 2600/156
USPC ....................................................... 424/204
See application file for complete search history.

(56) References Cited

U.S. PATENT DOCUMENTS

| | | |
|---|---|---|
| 6,440,718 B1 | 8/2002 | Probst |
| 2004/0001864 A1 | 1/2004 | King et al. |

FOREIGN PATENT DOCUMENTS

| | | |
|---|---|---|
| EP | 1632247 A1 | 3/2006 |
| JP | 2009505674 A | 2/2009 |
| RU | 2143921 C1 | 1/2000 |
| WO | WO-2007/027106 A1 | 3/2007 |

OTHER PUBLICATIONS

Abrams et al., Assembly of foot-and-mouth disease virus empty capsids synthesized by a vaccinia virus expression system, 1995, Journal of General Virology, 76:3089-3098.*
Cardno et al., A homogeneous cell-based bicistronic fluorescence assay for high-throughput identification of drugs that perturb viral gene recoding and read-through of nonsense stop codons, 2009, RNA, 15:1614-1621.*
Lewis et al., Expression, processing, and assembly of foot-and-mouth disease virus capsid structures in heterologous systems: induction of a neutralizing antibody response in guinea pigs, 1991, Journal of Virology, 65(12):6572-6580.*
Mayr et al., Development of replication-defective adenovirus serotype 5 containing the capsid and 3C protease coding regions of foot-and-mouth disease virus as a vaccine candidate, 1999, Virology, 263:496-506.*
Sweeney et al., Structural and mutagenic analysis of foot-and-mouth disease virus 3C protease reveals the role of the B-ribbon in proteolysis, 2007, Journal of Virology, 81(1):115-124.*
Adamson et al., Control of human immunodeficiency virus type-1 protease activity in insect cells expressing Gag-Pol rescues assembly of immature but not mature virus-like particles, Virology, 308:157-65 (2003).
Baril et al., Efficiency of a programmed -1 ribosomal frameshift in the different subtypes of the human immunodeficiency virus type 1 group M, RNA, 9:1246-53 (2003).
Brunelle et al., Replacement of murine leukemia virus readthrough mechanism by human immunodeficiency virus frameshift allows synthesis of viral proteins and virus replication, J. Virol., 77(5):3345-50 (2003).
Cao et al., Synthesis of empty capsid-like particles of Asia I foot-and-mouth disease virus in insect cells and their immunogenicity in guinea pigs, Veterinary Microbiology, 137:10-7 (2009).
Cardno et al., A homogeneous cell-based bicistronic fluorescence assy for high-throughput identification of drugs that perturb viral gene recoding and read-through of nonsense stop codons, RNA (Cold Spring Harbor), 15(8):1614-21 (2009).
Chen et al., Characterization of RNA elements that regulate Gag-Pol ribosomal frameshifting in equine infectious anemia virus, J. Virol., 77(19):10280-7 (2003).

(Continued)

*Primary Examiner* — Stacy B. Chen
*Assistant Examiner* — Barry A Chestnut
(74) *Attorney, Agent, or Firm* — Marshall, Gerstein & Borun LLP

(57) ABSTRACT

The present invention provides a construct which, when expressed in a host cell, is capable of producing empty virus capsids, the construct comprising: (i) a nucleotide sequence encoding a capsid precursor protein; (ii) a nucleotide sequence encoding a protease capable of cleaving the capsid precursor protein; and (iii) a control element which controls the expression of the protease such that, when the construct is present in the host cell, the control element causes the protease to be expressed at a level sufficient to cleave the capsid precursor protein, but not sufficient to induce significant toxicity in the host cell. The invention also provides a vector and a host cell comprising such a construct and their use to generate empty virus capsids.

17 Claims, 10 Drawing Sheets

(56) References Cited

OTHER PUBLICATIONS

Curry et al., Foot-and-mouth disease virus 3C protease: recent structural and functional insights into an antiviral target, Int. J. Biochem. & Cell Biol., 39:1-6 (2007).

Dinman et al., The frameshift signal of HIV-1 involves a potential intramolecular triplex RNA structure, PNAS, 99(8):5331-6 (2002).

Giedroc et al., Frameshifting RNA pseudoknots: structure and mechanism, Virus Res., 139(2):193-208 (2009).

Harger et al., An in vivo dual-luciferase assay system for studying translational recoding in the yeast *Saccharomyces cerevisiae*, RNA, 9:1019-24 (2003).

Hughes, Phylogeny of the picornaviridae and differential evolutionary divergence of picornavirus proteins, Infect. Genet. Evol., 4:143-52 (2004).

International Preliminary Report on Patentability for corresponding International Application No. PCT/GB2010/001807, dated Apr. 24, 2012.

International Search Report and Written Opinion for corresponding International Application No. PCT/GB2010/001807, mailing date Aug. 16, 2011.

Knowles et al., Outbreak of foot-and-mouth disease virus serotype O in the UK caused by a pandemic strain, Veterinary Record, 148:258-9 (2001).

Ko et al., Noninfectious Virus-like particle antigen for Detection of Swine Vesicular Disease Virus Antibodies in Pigs by Enzyme-Linked Immunosorbent Assay, Clinical and Diagnostic Laboratory Immunology, 12(8):922-9 (2005).

Lewis et al., Expression, processing, and assembly of foot-and-mouth disease virus capsid structures in heterolgous systems: Induction of a neutralizing antibody response in guinea pigs, J. Virol., 65(12): 6572-80 (1991).

Li et al., Expression of Foot-and-Mouth Disease Virus Capsid Proteins in Silkworm-Baculovirus Expression System and Its Untilization as a Subunit Vaccine, PloS One, 3(5):e2273 (2008).

Mayr et al., Development of Replication-Defective Adenovirus Serotype 5 Containing the Capsid and 3C Protease Coding Regions of Foot-and-Mouth Disease Virus as a Vaccine Candidate, Virology, 263(2):496-506 (1999).

Moffat et al., Effects of foot-and-mouth disease virus nonstructural proteins on the structure and function of the early secretory pathway: 2BC but not 3A blocks endoplasmic reticulum-to-Golgi transport, J Virol., 79:4382-95 (2005).

Moffat et al., Inhibition of the secretory pathway by foot-and-mouth disease virus 2BC protein is reproduced by coexpression of 2B with 2C, and the site of inhibition is determined by the subcellular location of 2C, J Virol., 81:1129-39 (2007).

Sorensen al., Blocking Elisas using the FMDV non-structural proteins 3D, 3AB, and 3ABC produced in the baculorvirus expression system, Veterinary Quarterly, 20(suppl 2): s17-20 (1998).

Sweeney et al., Structural and mutagenic analysis of foot-and-mouth disease virus 3C protease reveals the role of the beta-ribbon in proteolysis, J. Virol., 81:115-24 (2007).

Viswanathan et al., Comparative studies on immunoreactivity of truncated recombinant proteins of foot and mouth disease virus (FMDV) produced in *E. coli* and insect cells, Ind.J. Exp. Biol., 37:536-40 (1999).

\* cited by examiner

```
      4261 CTACACCGCG CCACACCGCG TGTTGGCAAC AGTGTACAAC GGGACGAGCA AGTACTCCGC
           GATGTGGCGC GGTGTGGCGC ACAACCGTTG TCACATGTTG CCCTGCTCGT TCATGAGGCG
```

·2 Ala Gly Gly Thr Gly Arg Arg Gly Asp Leu Gly Pro Leu Ala  Ala Arg Val Ala Ala Gln Leu
```
      4321 AGGTGGTACG GGCAGACGGG GCGACCTAGG GCCTCTCGCG GCGAGGGTCG CCGCTCAGCT
           TCCACCATGC CCGTCTGCCC CGCTGGATCC CGGAGAGCGC CGCTCCCAGC GGCGAGTCGA
```

·2 Leu Pro Ala Ser Phe Asn Phe Gly Ala Ile Gln Ala Thr Thr  Ile His Glu Leu Leu Val Arg
```
      4381 TCCTGCTTCT TTCAACTTTG GTGCAATTCA AGCCACGACC ATCCACGAGC TCCTCGTGCG
           AGGACGAAGA AAGTTGAAAC CACGTTAAGT TCGGTGCTGG TAGGTGCTCG AGGAGCACGC
```

·2 Arg Met Lys Arg Ala Glu Leu Tyr Cys Pro Arg Pro Leu Leu  Ala Val Glu Val Ser Ser Gln
```
      4441 CATGAAGCGT GCCGAACTCT ACTGCCCCAG ACCACTGTTG GCAGTGGAGG TGTCGTCTCA
           GTACTTCGCA CGGCTTGAGA TGACGGGGTC TGGTGACAAC CGTCACCTCC ACAGCAGAGT
```

·2 Gln Asp Arg His Lys Gln Lys Ile Ile Ala Pro Ala Lys Gln  Leu Leu Asn Phe Asp Leu Leu
```
      4501 AGACAGACAC AAACAGAAGA TCATTGCACC TGCAAAACAA CTTTTGAACT TCGATTTGCT
           TCTGTCTGTG TTTGTCTTCT AGTAACGTGG ACGTTTTGTT GAAAACTTGA AGCTAAACGA
```
                                          SmaI
                                          XmaI
                                   AvaI          NotI
·2 Leu Lys Leu Ala Gly Asp Val Glu Ser Asn Pro Gly Pro Ser Gly Arg Gly Pro Phe Leu Gly
·1                                                                        Phe Arg
```
      4561 CAAGTTGGCA GGAGACGTTG AGTCCAACCC CGGGCCCAGC GGCCGCGGAC CTTTTTTAGG
           GTTCAACCGT CCTCTGCAAC TCAGGTTGGG GCCCGGGTCG CCGGCGCCTG GAAAAAATCC
```
·2 Gly Lys Ile Trp Pro Ser Tyr Lys Gly Arg Pro Gly Asn Phe Leu Thr Arg Asp Arg ···
·1       Glu Asp Leu Ala Phe Leu Gln Gly Lys Ala Arg Glu Phe Ser Tyr Glu Gly Pro Val Lys
```
      4621 GAAGATCTGG CCTTCCTACA AGGGAAGGCC AGGGAATTTT CTTACGAGGG ACCGGTGAAG
           CTTCTAGACC GGAAGGATGT TCCCTTCCGG TCCCTTAAAA GAATGCTCCC TGGCCACTTC
```
·1 Lys Pro Val Ala Leu Lys Val Lys Ala Lys Asn Leu Ile Val Thr Glu Ser Gly Ala Pro
```
      4681 AAGCCTGTCG CTTTGAAAGT GAAAGCTAAG AACTTGATTG TCACTGAGAG TGGAGCCCCA
           TTCGGACAGC GAAACTTTCA CTTTCGATTC TTGAACTAAC AGTGACTCTC ACCTCGGGGT
```
·1 Pro Thr Asp Leu Gln Lys Met Val Met Gly Asn Thr Lys Pro Val Glu Leu Ile Leu Asp
```
      4741 CCGACCGACT TGCAAAAGAT GGTCATGGGC AACACCAAGC CTGTTGAGCT CATCCTCGAC
           GGCTGGCTGA ACGTTTTCTA CCAGTACCCG TTGTGGTTCG GACAACTCGA GTAGGAGCTG
```
·1 Gly Lys Thr Val Ala Ile Cys Cys Ala Thr Gly Val Phe Gly Thr Ala Tyr Leu Val Pro
```
      4801 GGGAAGACGG TGGCCATTTG TTGTGCTACC GGAGTGTTTG GCACTGCGTA CCTCGTGCCT
           CCCTTCTGCC ACCGGTAAAC AACACGATGG CCTCACAAAC CGTGACGCAT GGAGCACGGA
```
·1 Arg His Leu Phe Ala Glu Lys Tyr Asp Lyr Ile Met Leu Asp Gly Arg Ala Met Thr Asp
```
      4861 CGTCATCTTT TTGCAGAAAA ATATGACAAG ATCATGCTGG ACGGCAGAGC CATGACAGAC
```

CONSTRUCT FOR PRODUCING EMPTY VIRUS CAPSIDS

This application is the U.S. National Stage of International Application No. PCT/GB2010/001807, incorporated by reference, filed Sep. 24, 2010, which claims the priority benefit of Great Britain Application No. 0918375.7, filed Oct. 20, 2009.

FIELD OF THE INVENTION

The present invention relates to a construct which, when expressed in a host cell, is capable of producing empty virus capsids, in particular empty foot and mouth disease virus (FMDV) capsids. The present invention also relates to vectors and host cells comprising such constructs.

BACKGROUND TO THE INVENTION

Foot and Mouth Disease (FMD)

FMD is a highly contagious and economically devastating disease of cloven-hoofed animals (Artiodactyla), affecting domesticated ruminants, pigs and a large number of wildlife species.

FMD is widely distributed throughout the world. Developed regions such as the continents of North and Central America and Antarctica, and countries such as Australia and New Zealand are free from disease while FMD is endemic in many developing countries such as those in sub-Saharan Africa, the Middle East, southern Asia, Southeast Asia and South America. There are also some areas of the world which are normally free from disease, such as Europe where FMD was eradicated in 1989 and where vaccination has ceased since 1991. However, there have been occasional incursions of disease such as the 2001 UK/EIRE/France/Netherlands epidemic due to a PanAsian O strain (Knowles et al., (2001) Veterinary Record. 148. 258-259) and the 2007 UK outbreak of serotype O1 BFS/1967.

The causal agent of FMD is Foot-and-Mouth Disease Virus (FMDV), a positive sense, single stranded RNA virus of the Picornaviridae family. FMDV exists as seven antigenically distinct serotypes namely A, O, C, Asia 1 and South African Territories (SAT) 1, 2 and 3, with numerous subtypes within each serotype.

Translation of the single-stranded RNA yields a polyprotein that is subsequently processed by virus-encoded proteases to produce the structural and non-structural proteins required for virus assembly and replication. The Leader (L) protease cleaves itself in cis or in trans at its C terminus from the P1-2A capsid precursor. The 2A protease cleaves itself at its C terminus to release P1-2A from P2. Processing of the P1-2A is effected by the 3C protease to produce the capsid proteins 1AB (also known as VP0), 1C (VP3) and 1D (VP1). In the virion, cleavage of 1AB occurs to produce 1A (VP4) and 1B (VP2).

FMDV Vaccines

Conventional vaccines against FMD consist of whole virus virions that have been chemically inactivated, normally by use of an aziridine such as binary ethyleneimine (BEI).

Inactivated whole virus vaccines play a key role in campaigns to control and eradicate FMD. However, vaccines produced from viral tissue culture are associated with the risk of virus release during vaccine production. There is also the risk of improper inactivation of the virus which has the potential to lead to vaccine-related FMD outbreaks.

In order to reduce these risks, the possibility of using empty capsid-like particles of FMDV has been considered. Such particles comprise the structural proteins of FMDV but are non-replicative and non-infectious because they have no RNA genome. As the external structure of the empty capsids should be the same as the wild-type virus, empty capsids should be similarly antigenic and immunogenic.

Several attempts have been made to produce empty FMD capsid particles, but there have been recurring problems associated with yield and stability of the product.

A vaccinia virus expression system has been used to express a P1-2A-3C cassette (Abrahams et al (1995) J. Gen Virol. 76:3089-3098). It was found that constitutive expression of the cassette was unsuccessful but vv/FMDV recombinants could be isolated when the cassette was placed under the control of the bacteriophage T7 promoter. However, such a system could not be used for prolonged expression of empty capsids because after time, the toxicity of the P1-2A-3C cassette would prevail. There is also the issue that constant T7 Pol expression would be needed to drive production of the P1-2A-3C. It may be possible to achieve this at small scale in tissue culture, but it would be not be possible to extrapolate this to a manufacturing scale. Moreover, products produced in a vaccinia system are not commercially viable for a medical or veterinary application.

Li et al (2008) (PLoS ONE 28:3(5) e2273) report the expression of FMDV virus capsid proteins in a silkworm-baculovirus expression system. Recombinant virus expressing the intact coding regions of P1-2A and 3C were used to inoculate silkworms and subsequently the haemolymph collected from the dying silkworms. It was shown that a preparation of these "expressed antigens" caused an anti-FMDV-antibody response in cattle. However, the nature of the "expressed antigens" is entirely unclear, and the authors appear to assume it is a "subunit vaccine" as opposed to an empty capsid.

Cao et al ((2009) Veterinary Microbiology 137:10-17) describes a recombinant baculovirus system which simultaneously expresses the genes for the P12A and 3C proteins of FMDV from individual promoters. It was shown by Western blotting that the capsid proteins were processed to some extent by 3C protease and that empty capsid particles could be observed by immunoelectron microscopy. Immunisation with a crude extract of empty capsid did produce an immune response, but the levels of FMDV-specific antibodies and neutralising antibodies were lower that the conventional inactivated vaccine. It is predicted that this is due to lower levels of empty capsid particles. It is concluded that further studies are needed to improve the amount of protein expression and empty capsid assembly in insect cells.

There is thus a need for an improved method for producing empty virus capsids which produces an immunogenic, stable product at a reasonable yield.

SUMMARY OF ASPECTS OF THE INVENTION

The present inventors have surprisingly found that the reason for the low yield which has historically been associated with FMDV empty capsid production is that the level of 3C protease is too high in the host cell, which causes toxicity. In order to produce empty capsid particles at high yield, it is necessary to balance the expression and/or activity of the 3C protease, so that it is expressed/active enough to cleave the capsid protein precursor but not expressed/active at levels which induce toxicity in the host cell.

Thus, in a first aspect, the present invention provides a construct which, when expressed in a host cell, is capable of producing empty virus capsids, the construct comprising:

(i) a nucleotide sequence encoding a capsid precursor protein;
(ii) a nucleotide sequence encoding a protease capable of cleaving the capsid precursor protein; and
(iii) a control element which controls the expression of the protease such that, when the construct is present in the host cell, the control element causes the protease to be expressed at a level sufficient to cleave the capsid precursor protein, but not sufficient to induce significant toxicity in the host cell.

The control element may be derivable from a retrovirus, in particular the control element may be a retrovirus frameshift site, such as the HIV-1 frameshift site. The HIV-1 frameshift site causes a frameshift in about 5% of the mRNAs translated.

The frameshift site may be located between the nucleotide sequence encoding the capsid precursor protein and the nucleotide sequence encoding the protease, such that when the construct is translated:
(1) if the ribosome does not undergo a frameshift it produces a truncated product (which comprises the capsid precursor protein but not the protease); but
(2) if the ribosome does undergo a frameshift, both the capsid precursor protein and the protease are translated.

In the construct of the first aspect of the invention, the activity of the protease may also be reduced. For example, the protease may include at least one mutation which reduces its capsid precursor protein cleaving activity.

The protease (e.g. mutant protease) may have approximately 3-fold lower capsid precursor protein cleaving activity that the wild-type protease.

The empty capsids produced by a host cell comprising a construct according to the first aspect of the invention may be picomavirus capsids, such as Foot and Mouth Disease Virus (FMDV) capsids.

In order to produce empty FMDV capsids, the precursor protein may be P1 and the protease may be 3C. In order to reduce the activity of the 3C protease, it may comprise a mutation, for example at Cys142.

In a second aspect, the present invention provides a vector comprising a construct according to the first aspect of the invention. The vector may, for example, be a baculovirus transfer vector; a DNA vector, plasmid or a viral vector.

In a third aspect, the present invention provides a host cell comprising a construct according to the first aspect of the invention. In a first embodiment, the host cell may be capable of producing a vector in accordance with the second aspect of the invention. In a second embodiment, the host cell may be capable of producing empty virus capsids.

The host cell may, for example be an insect cell or a mammalian cell.

Further aspects of the invention relate to:
(i) a method for producing empty virus capsids by expressing a construct according to the first aspect of the invention in a host cell and harvesting empty virus capsids produced by the host cell;
(ii) a method for the production of a vaccine, by producing empty virus capsids by such a method and incorporating the empty virus capsids in a vaccine;
(iii) a method of treating and/or preventing a disease in a subject, by expressing a construct according the first aspect of the invention in the subject such that empty capsids are produced in vivo;
(iv) a construct according to the first aspect of the invention or a vector according to the second aspect of the invention for use in the prevention and/or treatment of a disease;
(v) the use of a construct according to the first aspect of the invention, or a vector according to the second aspect of the invention in the manufacture of a medicament for the prevention and/or treatment of a disease;
(vi) the use of a retroviral control element to control the expression of a picornavirus protein; and
(vii) a construct which comprises a nucleotide sequence encoding a picornavirus protein under the control of a retroviral control element.

"Empty capsid"-based vaccines are advantageous over traditional inactivated whole-pathogen vaccines (e.g. for FMD) because that do not require high-security containment facilities for manufacture, thus alleviating any risk of virus "escape". They are also non-infectious, easy to manipulate and (in view of the present invention) easy and inexpensive to prepare.

DESCRIPTION OF FIGURES

FIG. 4—Introduction of the HIV-1 frameshift sequence into the FMDV sequence. The P1 reading frame is the upper of the two and insertion results in truncation of the translated product at the stop codon marked in red. A −1 frameshift at the beginning of the inserted sequence (orange box) results in correction of the reading frame to include the 3C translation (lower frame).

A complete phylogeny and discussion can be found in: Hughes A L. (2004) *Phylogeny of the Picornaviridae and differential evolutionary divergence of picornavirus proteins*. Infect Genet Evol. 4:143-52.

Figure 1:
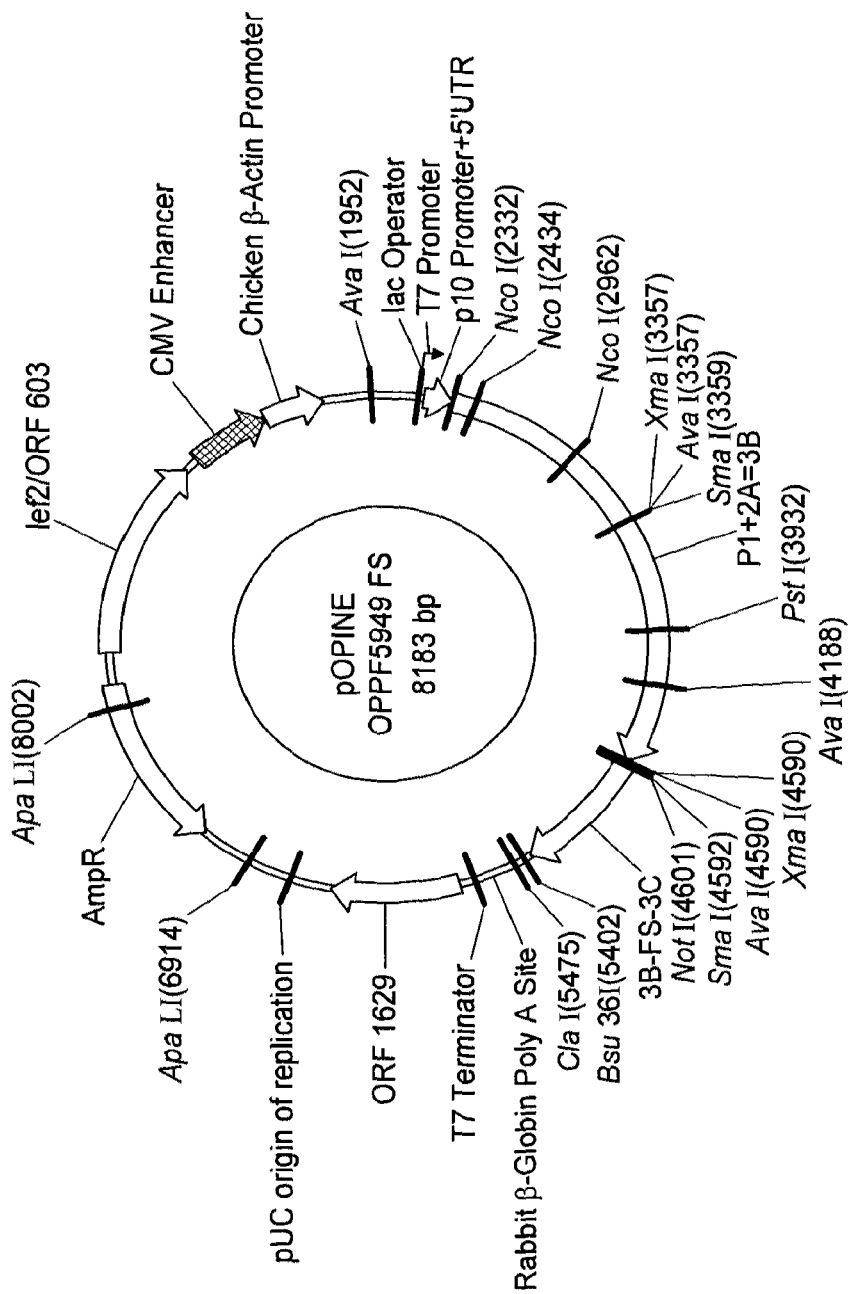
FIG. 1—The expression vector pOPINE5949-FS. The vector is a derivative of the commercial vector pTriEx1.1 (EMD Sciences) but has been amended for seamless cloning. The salient features of the vector and sites of diagnostic restriction sites are shown. A key step necessary for the successful expression of FMDV empty capsids is the introduction of a sequence encoding the HIV-1 frameshift site ahead of the 3C coding region between the unique NotI and Bsu36Irestriction sites. As a result, all mRNAs originating from the p10 or CMV promoter translate the P1 precursor protein but only a subset translate the 3C protease. When used to form a recombinant baculovirus the sequence between ORF603 clockwise to ORF1629 recombines with the virus genome. The P10 promoter is then activated as part of the baculovirus infectious cycle producing recombinant product in the infected cell.
Figure 7:
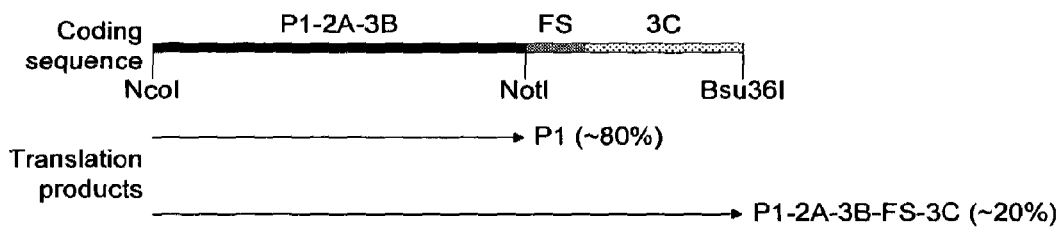

FIG. 7—The linear map of the expression cassette in FIG. 1 and its possible translation products. The suggested relative levels of translation for the P1 and P1-2A-3B-FS-3C product are taken from the literature and have not been determined empirically.

Figure 8:
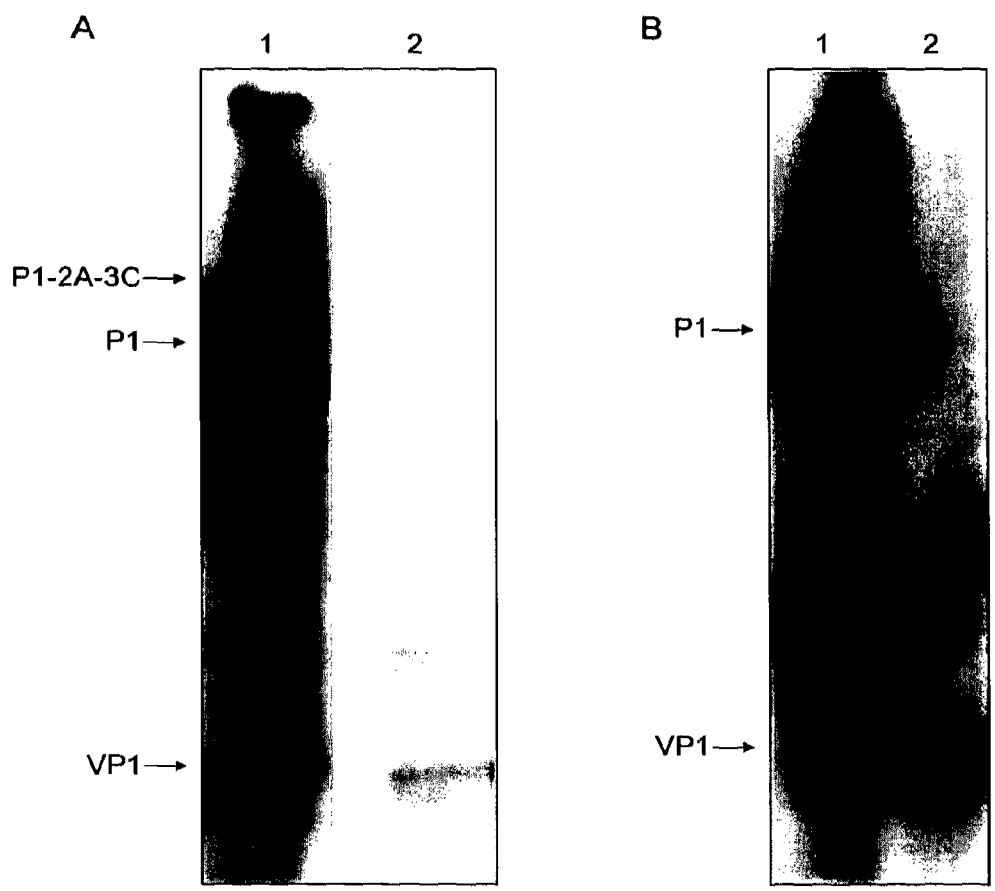

FIG. 8—Toxicity of the 3C protease. Insect cells infected with recombinant baculoviruses expressing the FMDV P1 coupled to 3C. In A track 1 is a mutant in the active site Cys at residue 163 and abundant synthesis of the P1-3C fusion protein which spontaneously degrades to P1 is apparent. Track 2 is the wild type protease; very little synthesis of P1 of the mature capsid protein VP1 is apparent. In B recombinant viruses_ expressing P1 (track 1) and P1 coupled to the attenuated 3C (track 2) are compared. Now high level synthesis is maintained and the P1 precursor is stoichiometrically converted to the mature capsid protein VP1. Cell lysates were resolved by 10% SDS-PAGE and the western blots were probed with a polyvalent FMDV antiserum in which most reactivity is against VP1. Molar amounts of VP0 and VP3 are also present but are not revealed by this serum.

Figure 9:
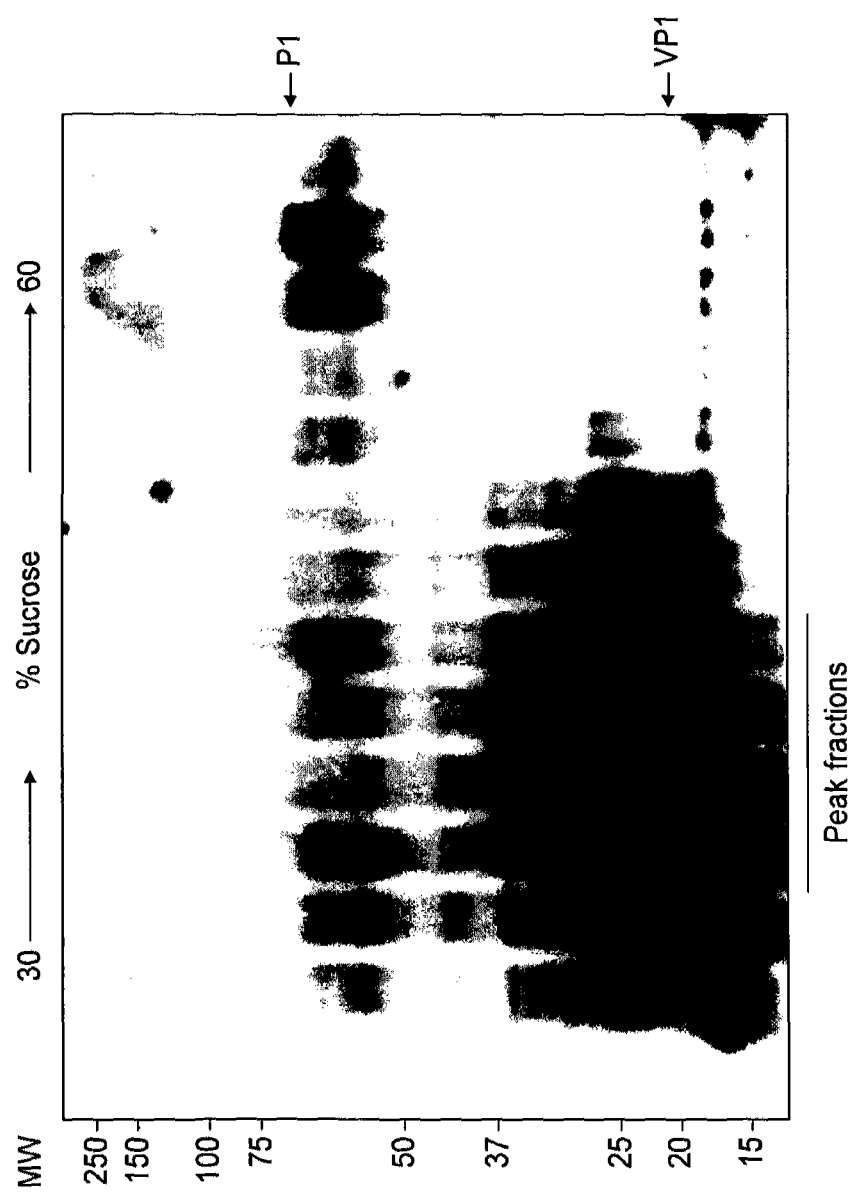

FIG. 9—Assembly of empty FMDV capsids. Sucrose gradient analysis of the expression products from recombinant baculovirus infected insect cells where modification of the 3C protease activity has been achieved. Some unprocessed P1 precursor, probably aggregated, is present at the bottom of the gradient whereas the VP1 cleavage product forms a strong broad peak in the 35-45% sucrose fractions. The position in the gradient is that expected of an assembled particle and not soluble antigen.

Figure 10:
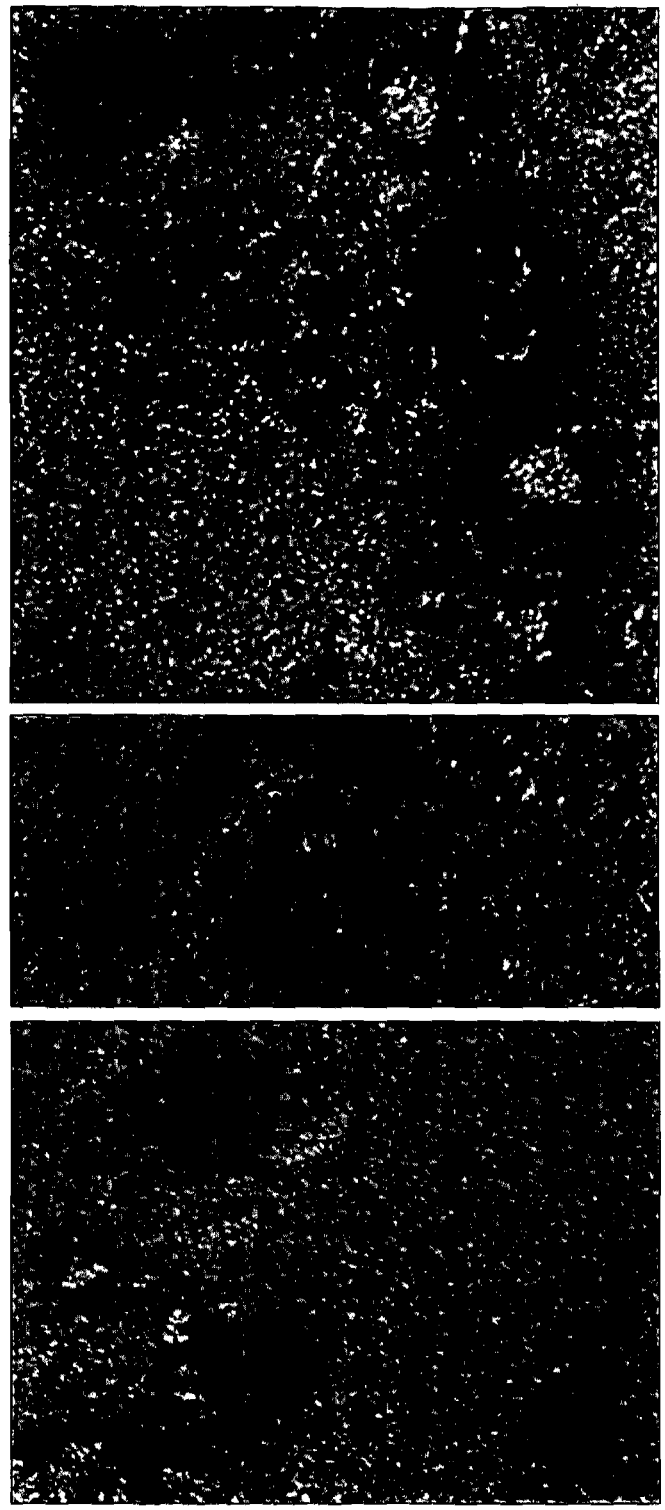

FIG. 10—Visualisation of empty FMDV A serotype capsids produced by baculovirus expression. Peak fractions from a sucrose gradient were pooled and concentrated before being adsorbed to carbon coated formvar grids and negatively stained with uranyl acetate. A number of particles with a diameter of 25 nm are seen (two arrowed). Note the stain inside the particle showing they are empty.

A particle showing particularly good angular definition consistent with an icosahedral structure is arrowed red.

Figure 11:
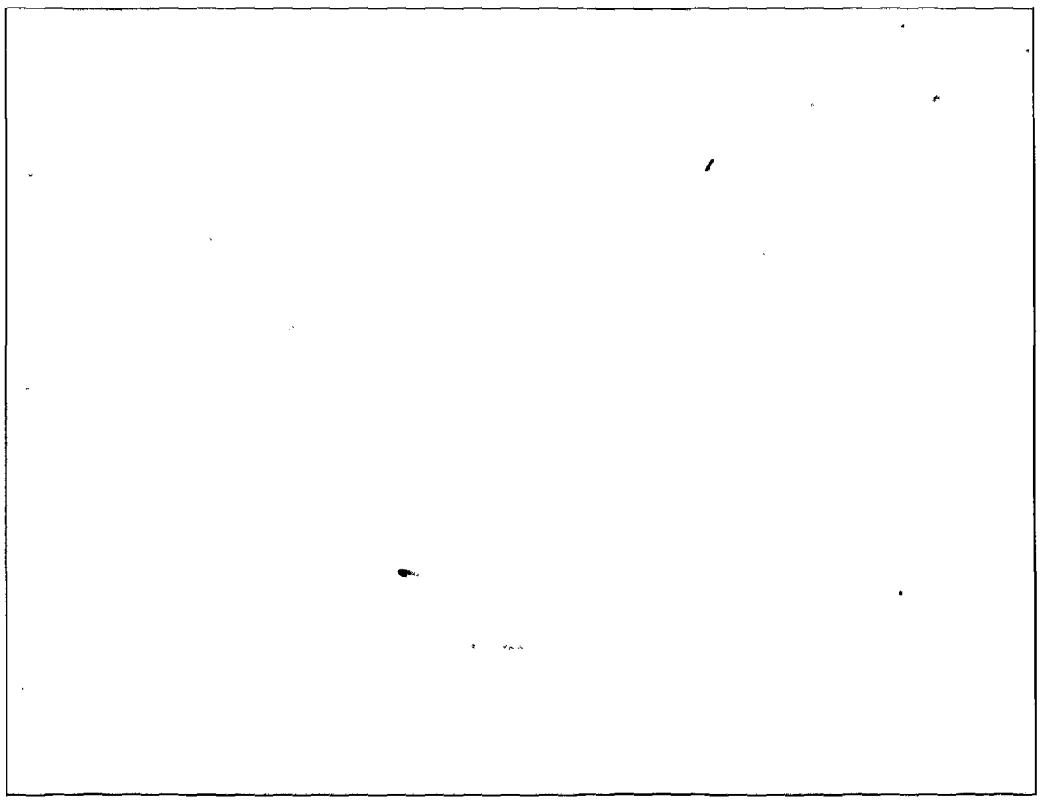

FIG. 11—Visualisation of empty FMDV O serotype capsids produced by baculovirus expression.

Figure 12:
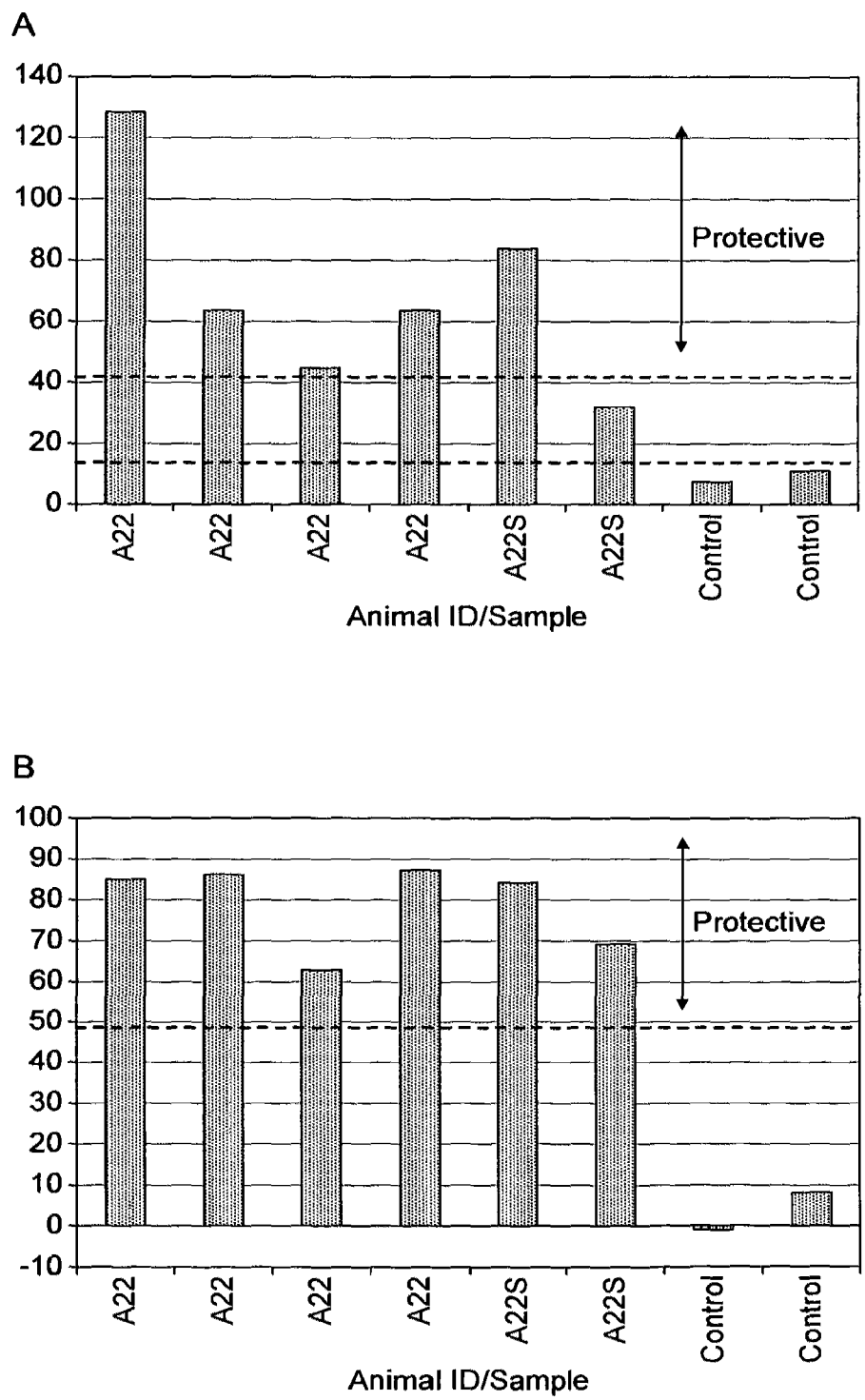

FIG. 12—A graph demonstrating the induction of specific antibodies in guinea pigs in response to immunisation with synthetic capsids. The antibody titres were measured using (A) a virus neutralization test, and (B) a liquid phase blocking ELISA. Immunisation of guinea pigs with the synthetic A serotype capsids results in the induction of antibody titres that are consistent with levels demonstrated to be protective in previous studies.

DETAILED DESCRIPTION

Construct

In a first aspect of the invention, the present invention provides construct which comprises
(i) a nucleotide sequence encoding a capsid precursor protein;
(ii) a nucleotide sequence encoding a protease capable of cleaving the capsid precursor protein; and
(iii) a control element which controls the expression of the protease.

The term "nucleotide sequence" includes an RNA or DNA sequence. It may be single or double stranded. It may, for example, be genomic, recombinant, mRNA or cDNA.

The construct may be a nucleotide sequence which comprises nucleotide sequences (i) and (ii), possibly in a contiguous manner. There may be a section of sequence between nucleotide sequences (i) and (ii). The control element may be present in that section of sequence, such that it controls expression of the protease but does not control or affect expression of the capsid precursor protein.

The construct may be present as part of a plasmid, transfer vector or host cell genome (see below).

Control Element

The construct of the first aspect of the invention comprises a control element which controls the expression of the protease. The control element may, for example, at least partly control transcription and/or translation of the protease.

Specifically, the control element causes the protease to be expressed at a level sufficient to cleave the capsid precursor protein, but not sufficient to induce significant toxicity in the host cell.

Cleavage of the capsid precursor protein may be analysed using techniques known in the art. For example, recombinant protein extracts from host cells may be separated by gel-electrophoresis and the separated proteins transferred on to a nitro-cellulose membrane for Western blotting. Western blotting with an anti-viral antibody should reveal the degree and extent of protease-mediated cleavage.

For example, for FMDV, the unprocessed capsid precursor protein (P1-P2A) would appear as a band of 81 kDa, and cleavage may produce VP31 (47 kDa), VP3 (24 kDa) and/or VP1 (24 kDa).

Cleavage of the capsid precurson protein can also be inferred by the production of empty capsids (see below).

The degree of cytotoxicity in the host cell induced by the protease may also be analysed using techniques known in the art. For example, trypan blue exclusion may be used e.g. by mixing equal volumes of 0.4% trypan blue with cells and defining the level of viability as measured by the Countess automated cell counter (Invitrogen).

The level of toxicity is not considered to be "significant" if less than 10%, less than 5% or less than 2% of the host cells are rendered non-viable by the protease. The level of toxicity is not considered to be "significant" if the host cell is capable of expressing the capsid precursor protein at 80, 90 or 95% of the level which would be achieved in the absence of the co-expression of the 3C protein (ignoring the effect of cleavage of the capsid precursor protein by the protease).

The control element may reduce the expression of the 3C protease, compared to the level of expression which would result if the control element were absent.

The control element may be a frameshift site which causes the translating ribosome to skip (or repeat) at least one base in a percentage of cases when reading an mRNA. During frameshifting, translating ribosomes may be induced to slide one nucleotide forward or backward at a distinct point in the transcript, with protein synthesis then continuing in the +1 or −1 reading frame, respectively.

Programmed −1 ribosomal frameshift signals are well characterised and some bacterial −1 frameshifting events have also been reported. A number of viruses infecting eukaryotic cells utilize programmed −1 ribosomal frameshifts, demonstrating that the cis elements involved in the frameshifting process are operational in eukaryotes. In viral systems, the efficiency of frameshifting is an essential determinant of the stoichiometry of synthesized viral protein products, which must be rigidly maintained for efficient propagation of the virus.

Human immunodeficiency virus (HIV) −1 uses ribosomal frameshifting to produce the required ratio of Gag and Gag-Pol polyproteins. The stem-loop structure of the frameshift signal is thought to impede the ribosome and cause slippage in the 5' direction, this causes the −1 frameshift and translation then continues in the new frame (see FIG. 3).

The control element may cause a frameshift in between 1-20%, 1-10%, 3-7% or about 5% of the mRNAs translated.

The frameshift sequence may comprise a run of about 6 uracils, where slippage occurs, followed by a sequence capable of forming a pseudoknot which causes the ribosome to pause, promoting the slip.

The control element may be upstream of the protease-encoding nucleotide sequence and downstream of the capsid precursor protein encoding sequence.

Empty Capsids

An "empty capsid" is an entity which comprises the protein shell of a virus but lacks the RNA or DNA genome. An empty capsid should be antigenic and immunogenic in the same way as the wild-type vaccine because it retains the same structural epitopes, but it should produce no infection, due to the lack of the genome.

The production of empty capsid may be investigated or verified using techniques known in the art such as sucrose density centrifugation or electron microscopy (Abrahams et al (1995) as above).

Monoclonal antibodies may be used specific for conformational epitopes on the wild type virus in order to investigate whether the antigenicity of the empty capsid is retained.

Protease

The protease may be any viral protease which cleaves a capsid precursor protein as a step of the production and assembly of capsids.

As mentioned above, for picornaviruses, such as FMDV, proteolytic processing of the precursor P1 into VP0 (VP2 plus VP4), VP3 and VP1 occurs by means of the viral protease 3C or its precursor 3CD.

The sequence of FMDV wild-type 3C protease from an FMDV type A strain is given below:

1 sgapptdlqk mvmgntkpve lildgktvai ccatgvfgta ylvprhlfae kydkimldgr

61tmtdsdyrvf efeikvkgqd mlsdaalmvl hrgnrvrdit khfrdvarmk kgtpvvgvin 121 nadvgrlifs gealtykdiv vcmdgdtmpg lfaykaatka gycggavlak dgaetfivgt 181 hsaggngvgy cscvsrsmlf kmkahidpep hhe The crystal structure of the 3C protease has been elucidated and mutagenic analysis carried out to provide information on the active site (Sweeney et al (2007) J. Virol. 81:115-124).

The construct of the first aspect of the invention may include at least one mutation which reduces its capsid precursor protein cleaving activity.

The mutation may, for example, be in the active site of the protease. There is thought to be a catalytic triad in the active site made up of residues 163, 46 and 84. The mutation may involve deletion or substitution of one or more of these residues. The mutation should reduce but not abolish the capsid precursor protein cleaving activity.

The crystal structure of the 3C protease revealed that there is a β-ribbon that folds over the peptide-binding cleft and contributes to substrate recognition (Sweeney et al (2007) as above). The mutation may, for example, be in the β-ribbon (residues 138 to 150). The mutation may, for example, be a substitution at residue 142. The mutation may be a C142V, C142A or a C142T mutation. The mutation may be a C142T mutation.

The mutation may reduce the specificity constant for the enzyme by between 3-fold and 2-fold, or 3-fold and 1.5 fold. For example if the specificity constant for the wild-type enzyme is 990 $k_{cat}$/Km, the specificity constant for the mutant enzyme may be between 495 and 330, or between 660 and 330 $k_{cat}$/Km.

The mutant protease may have 10-50%, 20-40% or about 30% of the capsid precursor protein cleaving activity that the wild-type protease.

Capsid Precursor Protein

The capsid precursor protein may (for picornaviruses) be P1, which is cleaved by the 3C protease into VP0, VP3 and VP1.

Alternatively the capsid precursor protein may be P1-2A. The 2A protease cleaves itself at its C terminus to release P1-2A from P2.

The capsid precursor protein may be cleavable by the protease to form (part of an) empty capsid. The precursor protein may comprise all the types of protein necessary to form an empty capsid, which are producible by protease cleavage.

Vector

In a second aspect, the present invention provides a vector comprising a construct according to the first aspect of the invention.

The vector may, for example, be a plasmid, or a baculovirus transfer vector, a DNA vector or a viral vector.

The vector may be capable of transferring the construct to a host cell.

The vector may be capable of transferring the construct to a plant, insect, or animal cell.

The baculovirus expression system is extensively used for the production of viruses and virus-like particles.

The vector of the present invention may, for example, be one or more transfer plasmid(s) used to transform cells (e.g. *E. coli* cells) in which the baculovirus shuttle vector is propagated.

The construct of the first aspect of the invention may be or comprise recombinant baculovirus DNA generated by site-specific transposition of DNA from the transfer vector into a baculovirus shuttle vector (bacmid). This DNA may be transfected into insect cells to produce recombinant baculovirus.

The vector of the present invention may be the resultant recombinant baculovirus.

Other viral vectors include but are not limited to adenoviral vectors, adeno-associated viral (AAV) vectors, herpes viral vectors, retroviral vectors (including lentiviral vectors).

Retroviruses are commonly used in gene therapy approaches. The recombinant retroviruses such as the Moloney murine leukemia virus have the ability to integrate into the host genome in a stable fashion. They contain a reverse transcriptase which allows integration into the host genome. Retroviral vectors have been used in a number of FDA-approved clinical trials such as the SCID-X1 trial.

The primary drawback to use of retroviruses such as the Moloney retrovirus involves the requirement for cells to be actively dividing for transduction. As a result, cells such as neurons are very resistant to infection and transduction by retroviruses.

Lentiviruses are a subclass of retroviruses. They have recently been adapted as gene delivery vehicles (vectors) due to their ability to integrate into the genome of non-dividing cells. The viral genome in the form of RNA is reverse-transcribed when the virus enters the cell to produce DNA, which is then inserted into the genome at a random position by the viral integrase enzyme. The vector, now called a provirus, remains in the genome and is passed on to the progeny of the cell when it divides.

For safety reasons lentiviral vectors never carry the genes required for their replication. To produce a lentivirus, several plasmids are transfected into a so-called packaging cell line, commonly HEK 293. One or more plasmids; generally referred to as packaging plasmids, encode the virion proteins, such as the capsid and the reverse transcriptase. Another plasmid contains the genetic material to be delivered by the vector. This plasmid is transcribed to produce the single-stranded RNA viral genome and is marked by the presence of the ψ (psi) sequence. This sequence is used to package the genome into the virion.

As opposed to lentiviruses, adenoviral DNA does not integrate into the genome and is not replicated during cell division. Their primary applications are in gene therapy and vaccination. Since humans commonly come in contact with adenoviruses, which cause respiratory, gastrointestinal and eye infections, they trigger a rapid immune response with potentially dangerous consequences. To overcome this problem scientists are currently investigating adenoviruses to which humans do not have immunity.

Adeno-associated virus (AAV) is a small virus which infects humans and some other primate species. AAV is not currently known to cause disease and consequently the virus causes a very mild immune response. AAV can infect both dividing and non-dividing cells and may incorporate its genome into that of the host cell. These features make AAV a very attractive candidate for creating viral vectors for gene therapy.

Host Cell

The present invention also provides a host cell comprising a construct of the first aspect of the invention.

The host cell may be capable of producing a vector (such as a viral vector) according to the second aspect of the invention.

The host cell may be a packaging cell or a producer cell, capable of producing a viral vector.

The host cell may be an Sf9 insect cell, capable of producing a recombinant baculovirus according to the second aspect of the invention.

The host cell may be capable of producing empty virus capsids.

The host cell may be a bacterial, insect, plant or animal cell.

Methods of Production

The present invention also provides a method for producing empty virus capsids which comprises the following steps:
  (i) expressing a construct according to the first aspect of the invention in a host cell; and
  (ii) harvesting empty virus capsids produced by the host cell.

The construct of the invention may be introduced in to the host cell by, for example transfection or transduction with a vector of the second aspect of the invention.

If the empty virus capsids are expressed outside the host cell, they may be harvested from the supernatant.

If the empty virus capsids are expressed inside the host cell, they may be harvested by, for example,
  (i) lysis of the host cells (for example by freeze-thawing); and optionally
  (ii) concentrated (e.g. by PEG-precipitation), and/or
  (iii) purification.

The present invention also provides a method for the production of a vaccine, which comprises the step of producing empty virus capsids by such a method and incorporating the empty virus capsids in a vaccine.

The vaccine may also comprise a pharmaceutically acceptable diluent, adjuvant or excipient.

Viruses

The present invention relates to the production of empty capsids of a particular virus.

The virus may, for example, be a picornavirus.

Examples of picornavirus genera, species and serotypes are given in Table 1:

TABLE 1

| Genus | Species (* signifies type species) | Serotypes |
|---|---|---|
| Enterovirus | Bovine enterovirus | two types: *bovine enterovirus* (BEV) 1 and BEV-2 |
| | Human enterovirus A | 21 types including some coxsackie A viruses and *enteroviruses* |
| | Human enterovirus B | 57 types including *enteroviruses*, coxsackie B viruses, echoviruses, and swine vesicular disease virus |
| | Human enterovirus C | 14 types including some coxsackie A viruses and *enteroviruses* |
| | Human enterovirus D | three types: EV-68, EV-70, EV-94 |
| | Poliovirus * | three types: poliovirus (PV) 1, PV-2 and PV-3 |
| | Porcine enterovirus A | one type: *porcine enterovirus* (PEV) 8 |
| | Porcine enterovirus B | two types: PEV-9 and PEV-10 |
| | Simian enterovirus A | one type: *simian enterovirus* (SEV) A1 |
| Rhinovirus | Human rhinovirus A * | 74 serotypes |
| | Human rhinovirus B | 25 serotypes |
| | Human rhinovirus C | 7 serotypes |
| Hepatovirus (also classed as Heparnavirus) | Hepatitis A virus * | one serotype: Hepatitis A virus (HAV) |
| | Avian encephalomyelitis-like viruses | one type: avian encephalomyelitis virus (AEV) |
| Cardiovirus | Encephalomyocarditis virus * | one serotype: *encephalomyocarditis virus* (EMCV). Note: Columbia SK virus, Maus Elberfeld virus and Mengovirus are strains of EMCV. |
| | Theilovirus | five types: Theiler's murine encephalomyellitis virus (TMEV), Vilyuisk human encephalomyelitis virus (VHEV), Theiler-like virus (TLV) of rats, Saffold virus (SAFV) 1 and SAFV-2 |

TABLE 1-continued

| Genus | Species (* signifies type species) | Serotypes |
|---|---|---|
| Aphthovirus | Foot-and-mouth disease virus[2] * | seven serotypes: O, A, C, Southern African Territories (SAT) 1, SAT 2, SAT 3, and Asia 1 |
| | Equine rhinitis A virus | single serotype: equine rhinitis A virus (ERAV) |
| Parechovirus | Human parechovirus * | six types: Human parechovirus (HPeV) 1, HPeV-2, HPeV-3, HPeV-4, HPeV-5, HPeV-6 |
| | Ljungan virus | Possibly three types have been described |
| Erbovirus | Equine rhinitis B virus * | Three types: equine rhinitis B virus (ERBV) 1, ERBV-2, ERBV-3 |
| Kobuvirus | Aichi virus * | single serotype: Aichi virus (AiV) |
| | Bovine kobuvirus | Single serotype: bovine kobuvirus (BKV) |
| Teschovirus | Porcine teschovirus * | 11 serotypes: porcine teschovirus (PTV) 1 to PTV-11 |

There are also plant picornaviruses which have been classified into a superfamily Secoviridae containing the families Comoviridae (genera Comovirus, Fabavirus and Nepovirus), Sequiviridae (genera Sequivirus and Waikavirus) and a number of unassigned genera (Cheravirus, Sadwavirus and Torradovirus (type species Tomato torrado virus)).

The virus may be a bee virus, such as Israeli acute paralysis virus; Kashmir bee virus; Kakugo virus; Varroa Destructor Virus; Sacbrood Virus; Deformed Wing Virus. All such viruses have been linked with the loss of bee colonies, so there is need for a diagnostic test to determine the cause of the colony loss.

The virus may be an animal pathogen, such as FMDV or swine vesicular disease virus. The virus may be a human pathogens, such as Enterovirus 71 (which causes outbreaks of diarrhoea); Coxsackievirus B viruses (causing diabetes and myocarditis), or polio virus.

The production of empty capsids for viruses which (in their natural state) act as human or animal pathogens is important for the generation of vaccines and therapeutic compositions.

Vaccine

The term 'vaccine' as used herein refers to a preparation which, when administered to a subject, induces or stimulates a protective immune response. A vaccine can render an organism immune to a particular disease.

The vaccine may be used therapeutically, to treat an existing infection; or propylactically, to block or reduce the likelihood of infection and/or prevent or reduce the likelihood of contracting the disease.

A vaccine comprises one or more vaccinating entity(ies) and optionally one or more adjuvants, excipients, carriers and diluents.

The vaccine may also comprise, or be capable of expressing, another active agent, for example one which may stimulate early protection prior to the vaccinating entity-induced adaptive immune response. The agent may be an antiviral agent, such as type I interferon. Alternatively, or in addition, the agent may be granulocyte-macrophage colony-stimulating factor (GM-CSF).

The vaccinating entity may, for example, by the construct of the first aspect of the invention, the vector of the second aspect of the invention or an empty capsid produced by the host cell of the third aspect of the invention.

DNA vaccination has some advantages over protein-based vaccines. For example, a DNA vaccine results in endogenous expression of the antigen in vivo, allowing antigenic peptides to be presented to the immune system via both the MHC class I and II pathways, thereby priming not only CD4+ T-cells, but also CD8+ T-cells. DNA vaccines are thus able to induce both humoral and a strong cellular immune response. The use of plasmid DNA as a vaccine can also trigger the innate immune system of the host, through the unmethylated CpG motifs in the bacterial plasmid backbone and the Toll-like receptor 9 (TLR9).

The vaccine may lack the non-structural protein coding genes 2B and 2C which may interfere with cellular immune responses by down-regulating MHC and cytokine secretion (Moffat et al., (2005) J Virol. 79. 4382-95 and Moffat et al., (2007) J Virol. 81. 1129-39).

Many commercially available FMD vaccines are multivalent to provide cover against the different FMD serotypes. By the same token, the vaccine of the present invention may comprise a plurality of vaccinating entities, each directed at a different serotype and/or different subtypes within a given serotype.

Treating/Preventing Disease

The present invention also provides a method of treating and/or preventing a disease in a subject by administration of an effective amount of such a vaccine.

The term 'preventing' is intended to refer to averting, delaying, impeding or hindering the contraction of the disease. The vaccine may, for example, prevent or reduce the likelihood of an infectious virus entering a cell.

'Treating' as used herein refers to caring for a diseased subject, in order to ameliorate, cure or reduce the symptoms of the disease, or reduce or halt the progression of the disease. It also refers to treatment which renders the virally-infected subject non-infectious to other subjects.

The subject may be any animal or plant which is susceptible to the disease. The subject may be a human, insect (such as a bee), plant, mammal or other animal.

For FMD the subject may be a cloven-hoofed animal. FMD susceptible animals include cattle, sheep, pigs, and goats among farm stock, as well as camelids (camels, llamas, alpacas, guanaco and vicuña). Some wild animals such as hedgehogs, coypu, and any wild cloven-footed animals such as deer and zoo animals including elephants can also contract FMD.

Administration

Methods of non-viral gene delivery include using physical (carrier-free gene delivery) and chemical approaches (synthetic vector-based gene delivery). Physical approaches, including needle injection, electroporation, gene gun, ultrasound, and hydrodynamic delivery, employ a physical force that permeates the cell membrane and facilitates intracellular gene transfer. The chemical approaches use synthetic or naturally occurring compounds as carriers to deliver the nucleotide sequence into cells.

The most suitable delivery method will depend on the delivery system used to deliver the nucleotide sequence to a target cell. For example, for plasmid administration, the plasmid preparation may be administered intramuscularly, intradermally or a combination of the above.

Viral vectors may be administered to a subject by methods known in the art, such as direct injection.

Retroviral Control of a Picornaviral Protein

The present invention also relates to the use of a retroviral control element to control the expression of a picornavirus protein and to a construct which comprises a nucleotide sequence encoding a picornavirus protein under the control of a retroviral control element.

The retroviral control element may be a retroviral frameshift site, such as a frameshift site derivable from the HIV-1 frameshift site which controls Gag and Gag-pol expression in that virus.

The picornavirus protein may be a non-structural protein, such as a protease. The picornavirus protein may be capable of cleaving a capsid precursor protein. The picornavirus protein may be the 3C protease from a picornavirus or its precursor 3CD.

The invention will now be further described by way of Examples, which are meant to serve to assist one of ordinary skill in the art in carrying out the invention and are not intended in any way to limit the scope of the invention.

EXAMPLES

Example 1

Mutational Analysis of Protease 3C in a Vector in which its Expression is Under the Control of the p10 Promoter The baculovirus transfer vector pOPINE5949 encodes the FMDV capid precursor protein P1 followed by the FMDV 3C protease connected by a short spacer region (2A-3B3) under control of the strong p10 baculovirus promoter (FIG. 1). Most of the remainder of the FMDV genome is missing. When used to generate a recombinant baculovirus, the theoretical outcome is the expression of a P1-2A-3B3-3C fusion protein which would self-cleave to produce the mature capsid proteins VP1-4 (encoded by P1) and assemble into virus capsids. The actual outcome of infection with such a recombinant baculovirus is that very little product is produced.

Figure 2:
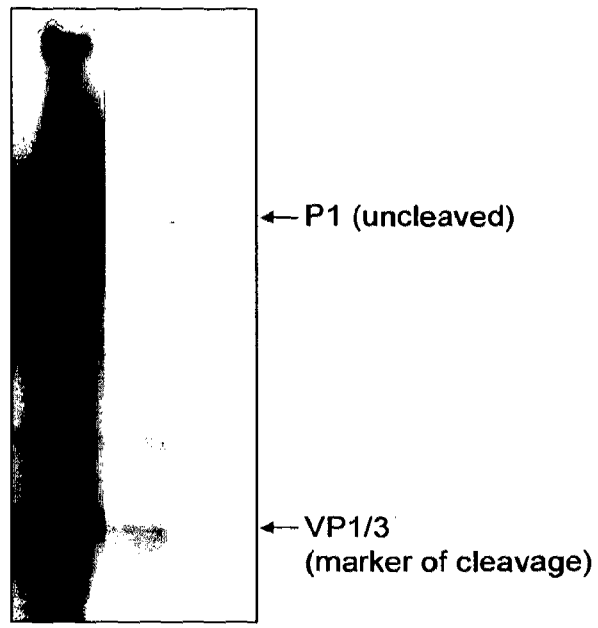
FIG. 2—Comparison of expression levels between recombinant baculoviruses that encode P1-2A-3B3-3C (right track) or P1-2A-3B3-3C$_{163S}$ (left track). Inactivation of 3C activity rescues abundant synthesis of P1.

This low amount of product is the result of 3C toxicity. This is illustrated by the fact that the inclusion, within pOPINE5949, of a single point mutation of the active site cysteine (Cys 163) of 3C allows the expression of copious amounts of the P1-2A-3B3-3C fusion protein (FIG. 2). This formally proves that 3C activity is a controlling feature of recombinant FMDV synthesis.

Methods

The Cys 163 mutation was introduced by standard site directed mutagenesis and then the mutant cassette was re-expressed.

Western Blotting

Protein samples were separated on pre-cast 10% Tris.HCl SDS-polyacrylamide gels (BioRad) and transferred to Immobilion-P membranes (Millipore) using a semi-dry blotter. Filters were blocked for one hour at room temperature using TBS containing 0.1% v/v Tween-20 (TBS-T), 5% w/v milk powder. Primary Guinea pig antibody against FMDV type A virus was used at a dilution of 1:1000 in PBS-T, 5% w/v milk powder for 1 hr at room temperature. Following several washes with TBS-T the membranes were incubated for 1 hour with HRP-conjugated anti-Guinea pig antibody and the bound antibodies detected by BM chemiluminescence (Roche).

Example 2

Figure 3:
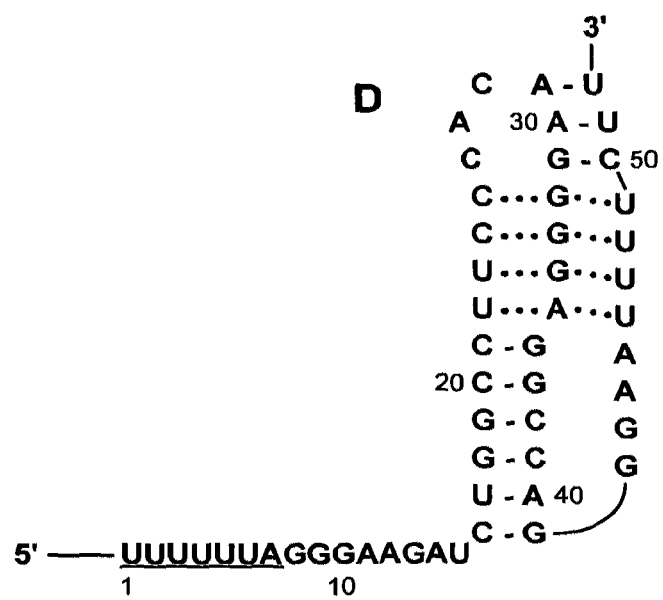
FIG. 3—The sequence used to cause a frameshift at the P1-3C junction. The key features are a run of uracils (underlined) where slippage occurs followed by a pseudoknot which causes the ribosome to pause so promoting the slip.

Production of a Construct in which 3C Protease Activity and Expression is Reduced To moderate the activity of the 3C protease between these two extremes, two approaches were combined, as follows:

1) introduction of a frameshift element in the 3B linker region between the sequences encoding P1 and 3C which causes a reduction in the amount of 3C synthesised; and 2) mutation of the 3C residue, Cys142, thus reducing the activity of 3C synthesised; and A frameshift element is a section of sequence which causes the translating ribosome to skip a base in a percentage of cases when reading an mRNA. A well described frameshift element is that described for the retrovirus HIV-1 which causes a −1 frameshift in about 5% of the mRNAs translated. The present inventors used the sequence defined by Dinman et al., (PNAS Apr. 16, 2002 vol. 99 no. 8 5331-5336 (FIG. 3).

The vector pOPINE5949-FS was thus constructed with the frameshift sequence inserted in the 3B3 linker region in such a way as to terminate the reading frame at this location. The insertion of the frameshift sequence interrupts the continuity of the P1-2A-3B3-3C mRNA such that the translated product is truncated in the 3B3 region and no 3C is produced (despite the downstream sequence encoding it being present in the message). However, a minus 1 frameshift by the ribosome in this region results in P1-2A-3B3-3C fusion protein expression by a subset of the mRNAs engaged by the ribosome (FIG. 4). If the frequency of the frameshift event is the same in insect cells as that measured in mammalian cells then the products of translation will be 95% P1-2A and 5% P1-2A-3B3-3C. There is thus a proportionately low level of synthesis of 3C protease.

Figure 5:
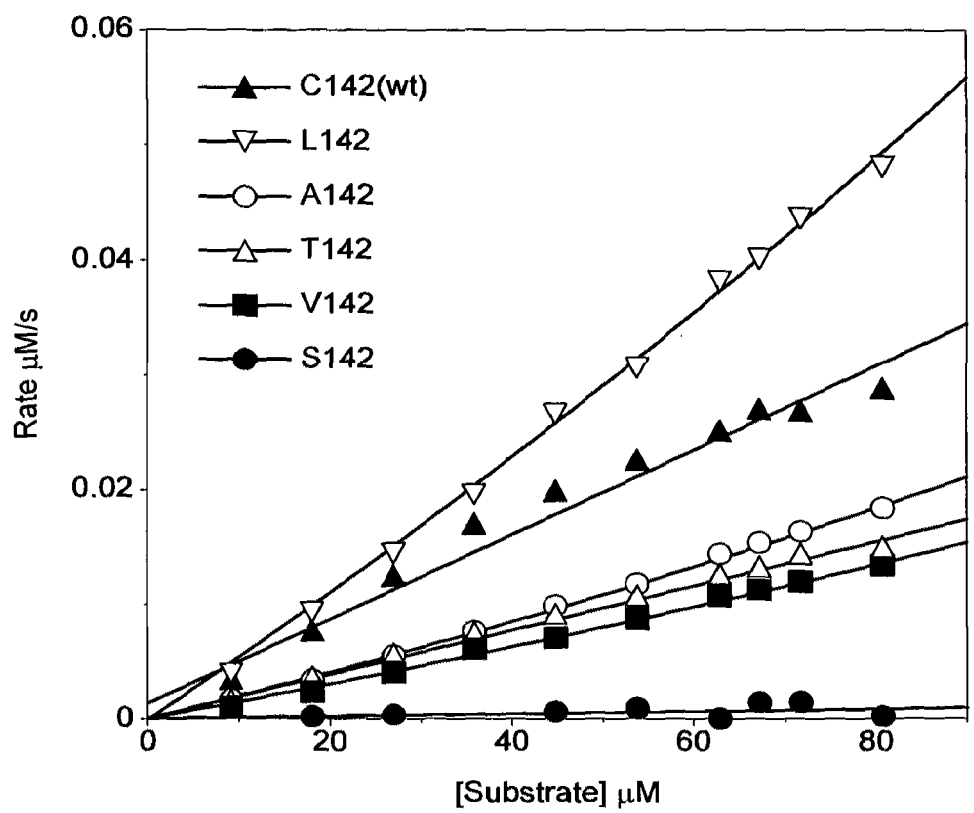
FIG. 5—In vitro activity measurements of 3C protease mutated at residue 142. Note that 142T and 142S both have reduced activity when compared to the parental sequence.
Figure 6:
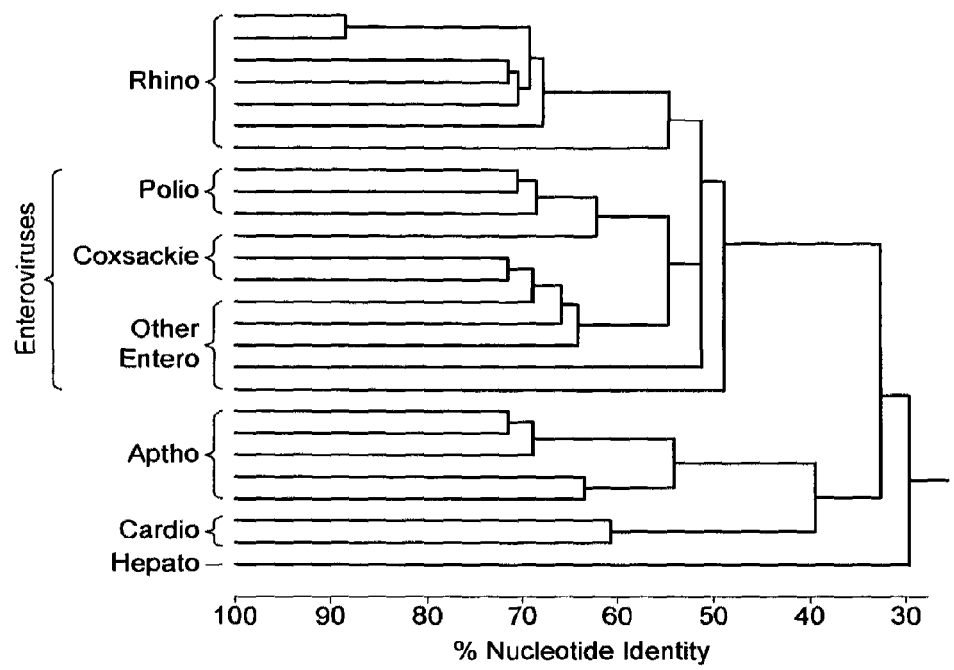
FIG. 6—Picornavirus phylogeny. The closely related family share a common coding strategy and replication cycle; what has been observed for the well studied viruses such as poliovirus (PV) and foot and mouth disease virus (FMDV) has held true for other members.

A recombinant baculovirus constructed using the pOPINE5949-FS sequence showed a cleavage pattern consistent with the generation of low levels of 3C protease (data not shown). However the overall level of synthesis still indicated some cytotoxicity and the activity of 3C was reduced further by site directed mutagenesis of the 3C sequence at position Cys 142 which has a role in enzyme activity (Sweeney et al (2007—as above)) (FIG. 5).

Example 3

Production of Cleaved VP1 Product and FMDV Empty Capsids

The combination of a frameshift and mutation of 142T in a recombinant baculovirus produced the desired level of P1 and 3C and resulted in substantial amounts of the cleaved VP1 product which assembled with other cleavage product to form the empty FMDV capsid.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in virology, molecular biology or related fields are intended to be within the scope of the following claims.

The invention claimed is:

1. A construct which, when expressed in a eukaryotic host cell, produces empty picornavirus capsids, the construct comprising: (i) a nucleic acid encoding a picornavirus capsid precursor protein; (ii) a nucleic acid encoding protease 3C, capable of cleaving the picornavirus capsid precursor protein, wherein the protease includes a mutation at Cys142 which reduces its capsid precursor protein cleaving activity; and (iii) a control element between the nucleic acid encoding the picornavirus capsid precursor protein and the nucleic acid encoding protease 3C which reduces expression of the protease compared to expression if the control element were absent such that, when the construct is present in the eukaryotic host cell, the control element causes the protease to be expressed at a level sufficient to cleave the picornavirus capsid precursor protein, but not sufficient to induce significant toxicity in the host cell, wherein the control element is a retrovirus frameshift site.

2. A construct according to claim 1, wherein the control element is the HIV-1 frameshift site.

3. A construct according to claim 1, wherein the control element causes a frameshift in about 5% of the mRNAs translated.

4. A construct according to claim 1 wherein the protease with the mutation has approximately 3-fold lower capsid precursor protein cleaving activity than wild-type protease 3C.

5. A construct according to claim 1 which, when expressed in a host cell, produces empty Foot and Mouth Disease Virus (FMDV) capsids.

6. A construct according to claim 5, wherein the picornavirus capsid precursor protein is P1.

7. A vector comprising the construct of claim 1.

8. A vector according to claim 7, which is a baculovirus transfer vector, a DNA vector, a plasmid vector or a viral vector.

9. An isolated host cell comprising the construct of claim 1.

10. An isolated host cell which produces a vector that comprises the construct of claim 1, said host cell comprising nucleic acid encoding virion proteins and a plasmid comprising the construct of claim 1.

11. An isolated host cell according to claim 9, which is capable of producing empty picornavirus capsids.

12. An isolated host cell according to claim 10 which is an insect cell or a mammalian cell.

13. A method for producing empty picornavirus capsids which comprises the following steps:

(i) expressing in a eukaryotic host cell a construct comprising:

(a) a nucleic acid encoding a picornavirus capsid precursor protein;

(b) a nucleic acid encoding a protease capable of cleaving the picornavirus capsid precursor protein, wherein the protease is a mutant 3C protease that includes a mutation at Cys142 which reduces its capsid precursor protein cleaving activity; and (c) a control element between the nucleic acid encoding the picornavirus capsid precursor protein and the nucleic acid encoding protease 3C which reduces expression of the protease compared to expression if the control element were absent such that, when the construct is present in the eukaryotic host cell, the control element causes the protease to be expressed at a level sufficient to cleave the picornavirus capsid precursor protein, but not sufficient to induce significant toxicity in the host cell, wherein the control element is a retrovirus frameshift site; and (ii) harvesting empty picornavirus capsids produced by the eukaryotic host cell.

14. The method according to claim 13 further comprising incorporating the empty picornavirus capsids in a vaccine.

15. A method of inducing an immune response in a subject, which comprises the step of expressing the construct of claim 1 in the subject such that empty picornavirus capsids are produced in vivo.

16. A method of inducing an immune response in a subject according to claim 15, wherein the construct is administered to the subject by DNA vaccination or using a viral vector.

17. A eukaryotic expression construct which comprises:

(i) a nucleic acid encoding a picornavirus capsid precursor protein;

(ii) a nucleic acid encoding protease 3C, capable of cleaving the picornavirus capsid precursor protein, wherein the encoded protease includes a mutation at Cys142 which reduces its capsid precursor protein cleaving activity, and (iii) a retrovirus frameshift site between the nucleic acid encoding the picornavirus capsid precursor protein and the nucleic acid encoding protease 3C such that, when the construct is translated: if the ribosome does not undergo a frameshift it produces a truncated product which comprises the picornavirus capsid precursor protein but not the protease; but if the ribosome does undergo a frameshift, both the picornavirus capsid precursor protein and the protease are translated.

\* \* \* \* \*

```
                        SEQUENCE LISTING

<160> NUMBER OF SEQ ID NOS: 6

<210> SEQ ID NO 1
<211> LENGTH: 213
<212> TYPE: PRT
<213> ORGANISM: Foot-and-mouth disease virus

<400> SEQUENCE: 1

Ser Gly Ala Pro Pro Thr Asp Leu Gln Lys Met Val Met Gly Asn Thr
1               5                   10                  15

Lys Pro Val Glu Leu Ile Leu Asp Gly Lys Thr Val Ala Ile Cys Cys
            20                  25                  30

Ala Thr Gly Val Phe Gly Thr Ala Tyr Leu Val Pro Arg His Leu Phe
        35                  40                  45

Ala Glu Lys Tyr Asp Lys Ile Met Leu Asp Gly Arg Thr Met Thr Asp
    50                  55                  60

Ser Asp Tyr Arg Val Phe Glu Phe Glu Ile Lys Val Lys Gly Gln Asp
65                  70                  75                  80

Met Leu Ser Asp Ala Ala Leu Met Val Leu His Arg Gly Asn Arg Val
                85                  90                  95

Arg Asp Ile Thr Lys His Phe Arg Asp Val Ala Arg Met Lys Lys Gly
            100                 105                 110

Thr Pro Val Val Gly Val Ile Asn Asn Ala Asp Val Gly Arg Leu Ile
        115                 120                 125

Phe Ser Gly Glu Ala Leu Thr Tyr Lys Asp Ile Val Val Cys Met Asp
130                 135                 140

Gly Asp Thr Met Pro Gly Leu Phe Ala Tyr Lys Ala Ala Thr Lys Ala
145                 150                 155                 160

Gly Tyr Cys Gly Gly Ala Val Leu Ala Lys Asp Gly Ala Glu Thr Phe
                165                 170                 175

Ile Val Gly Thr His Ser Ala Gly Gly Asn Gly Val Gly Tyr Cys Ser
            180                 185                 190

Cys Val Ser Arg Ser Met Leu Phe Lys Met Lys Ala His Ile Asp Pro
        195                 200                 205

Glu Pro His His Glu
    210

<210> SEQ ID NO 2
<211> LENGTH: 52
<212> TYPE: RNA
<213> ORGANISM: Artificial Sequence
<220> FEATURE:
<223> OTHER INFORMATION: Sequence used to cause a frameshift at the
      P1-3C junction

<400> SEQUENCE: 2
uuuuuuaggg aagaucuggc cuucccacaa ggggaggcca gggaauuuuc uu            52

<210> SEQ ID NO 3
<211> LENGTH: 660
<212> TYPE: DNA
<213> ORGANISM: Artificial Sequence
<220> FEATURE:
<223> OTHER INFORMATION: Introduction of HIV-1 frameshift sequence into
      FMDV sequence
```

<220> FEATURE:
<221> NAME/KEY: CDS
<222> LOCATION: (59)..(418)

<400> SEQUENCE: 3

```
ctacaccgcg ccacaccgcg tgttggcaac agtgtacaac gggacgagca agtactcc         58 gca ggt ggt acg ggc aga cgg ggc gac cta ggg cct ctc gcg gcg agg        106
Ala Gly Gly Thr Gly Arg Arg Gly Asp Leu Gly Pro Leu Ala Ala Arg
1               5                   10                  15 gtc gcc gct cag ctt cct gct tct ttc aac ttt ggt gca att caa gcc        154
Val Ala Ala Gln Leu Pro Ala Ser Phe Asn Phe Gly Ala Ile Gln Ala
                20                  25                  30 acg acc atc cac gag ctc ctc gtg cgc atg aag cgt gcc gaa ctc tac        202
Thr Thr Ile His Glu Leu Leu Val Arg Met Lys Arg Ala Glu Leu Tyr
            35                  40                  45 tgc ccc aga cca ctg ttg gca gtg gag gtg tcg tct caa gac aga cac        250
Cys Pro Arg Pro Leu Leu Ala Val Glu Val Ser Ser Gln Asp Arg His
50                  55                  60 aaa cag aag atc att gca cct gca aaa caa ctt ttg aac ttc gat ttg        298
Lys Gln Lys Ile Ile Ala Pro Ala Lys Gln Leu Leu Asn Phe Asp Leu
65                  70                  75                  80 ctc aag ttg gca gga gac gtt gag tcc aac ccc ggg ccc agc ggc cgc        346
Leu Lys Leu Ala Gly Asp Val Glu Ser Asn Pro Gly Pro Ser Gly Arg
                85                  90                  95 gga cct ttt tta ggg aag atc tgg cct tcc tac aag gga agg cca ggg        394
Gly Pro Phe Leu Gly Lys Ile Trp Pro Ser Tyr Lys Gly Arg Pro Gly
                100                 105                 110 aat ttt ctt acg agg gac cgg tga agaagcctgt cgctttgaaa gtgaaagcta      448
Asn Phe Leu Thr Arg Asp Arg
            115 agaacttgat tgtcactgag agtggagccc caccgaccga cttgcaaaag atggtcatgg      508 gcaacaccaa gcctgttgag ctcatcctcg acgggaagac ggtggccatt tgttgtgcta      568 ccggagtgtt tggcactgcg tacctcgtgc ctcgtcatct ttttgcagaa aaatatgaca      628 agatcatgct ggacggcaga gccatgacag ac                                    660
```

<210> SEQ ID NO 4
<211> LENGTH: 119
<212> TYPE: PRT
<213> ORGANISM: Artificial Sequence
<220> FEATURE:
<223> OTHER INFORMATION: Synthetic Construct

<400> SEQUENCE: 4

```
Ala Gly Gly Thr Gly Arg Arg Gly Asp Leu Gly Pro Leu Ala Ala Arg
1               5                   10                  15

Val Ala Ala Gln Leu Pro Ala Ser Phe Asn Phe Gly Ala Ile Gln Ala
                20                  25                  30

Thr Thr Ile His Glu Leu Leu Val Arg Met Lys Arg Ala Glu Leu Tyr
            35                  40                  45

Cys Pro Arg Pro Leu Leu Ala Val Glu Val Ser Ser Gln Asp Arg His
50                  55                  60

Lys Gln Lys Ile Ile Ala Pro Ala Lys Gln Leu Leu Asn Phe Asp Leu
65                  70                  75                  80

Leu Lys Leu Ala Gly Asp Val Glu Ser Asn Pro Gly Pro Ser Gly Arg
                85                  90                  95

Gly Pro Phe Leu Gly Lys Ile Trp Pro Ser Tyr Lys Gly Arg Pro Gly
                100                 105                 110
```

Asn Phe Leu Thr Arg Asp Arg
        115

<210> SEQ ID NO 5
<211> LENGTH: 660
<212> TYPE: DNA
<213> ORGANISM: Artificial Sequence
<220> FEATURE:
<223> OTHER INFORMATION: Introduction of HIV-1 frameshift sequence into
      FMDV sequence
<220> FEATURE:
<221> NAME/KEY: CDS
<222> LOCATION: (355)..(660)

<400> SEQUENCE: 5
ctacaccgcg ccacaccgcg tgttggcaac agtgtacaac gggacgagca agtactccgc    60
aggtggtacg ggcagacggg gcgacctagg gcctctcgcg gcgagggtcg ccgctcagct   120
tcctgcttct ttcaactttg gtgcaattca agccacgacc atccacgagc tcctcgtgcg   180
catgaagcgt gccgaactct actgccccag accactgttg gcagtggagg tgtcgtctca   240
agacagacac aaacagaaga tcattgcacc tgcaaaacaa ctttttgaact tcgatttgct   300 caagttggca ggagacgttg agtccaaccc cgggcccagc ggccgcggac cttt ttt     357
                                                              Phe
                                                               1 agg gaa gat ctg gcc ttc cta caa ggg aag gcc agg gaa ttt tct tac     405
Arg Glu Asp Leu Ala Phe Leu Gln Gly Lys Ala Arg Glu Phe Ser Tyr
        5                   10                  15 gag gga ccg gtg aag aag cct gtc gct ttg aaa gtg aaa gct aag aac     453
Glu Gly Pro Val Lys Lys Pro Val Ala Leu Lys Val Lys Ala Lys Asn
    20                  25                  30 ttg att gtc act gag agt gga gcc cca ccg acc gac ttg caa aag atg     501
Leu Ile Val Thr Glu Ser Gly Ala Pro Pro Thr Asp Leu Gln Lys Met
35                  40                  45 gtc atg ggc aac acc aag cct gtt gag ctc atc ctc gac ggg aag acg     549
Val Met Gly Asn Thr Lys Pro Val Glu Leu Ile Leu Asp Gly Lys Thr
 50                  55                  60                  65 gtg gcc att tgt tgt gct acc gga gtg ttt ggc act gcg tac ctc gtg     597
Val Ala Ile Cys Cys Ala Thr Gly Val Phe Gly Thr Ala Tyr Leu Val
                 70                  75                  80 cct cgt cat ctt ttt gca gaa aaa tat gac aag atc atg ctg gac ggc     645
Pro Arg His Leu Phe Ala Glu Lys Tyr Asp Lys Ile Met Leu Asp Gly
             85                  90                  95 aga gcc atg aca gac                                                 660
Arg Ala Met Thr Asp
        100

<210> SEQ ID NO 6
<211> LENGTH: 102
<212> TYPE: PRT
<213> ORGANISM: Artificial Sequence
<220> FEATURE:
<223> OTHER INFORMATION: Synthetic Construct

<400> SEQUENCE: 6

Phe Arg Glu Asp Leu Ala Phe Leu Gln Gly Lys Ala Arg Glu Phe Ser
1               5                   10                  15

Tyr Glu Gly Pro Val Lys Lys Pro Val Ala Leu Lys Val Lys Ala Lys
            20                  25                  30

Asn Leu Ile Val Thr Glu Ser Gly Ala Pro Pro Thr Asp Leu Gln Lys
        35                  40                  45

Met Val Met Gly Asn Thr Lys Pro Val Glu Leu Ile Leu Asp Gly Lys

-continued

```
            50                  55                  60
Thr Val Ala Ile Cys Cys Ala Thr Gly Val Phe Gly Thr Ala Tyr Leu
65                  70                  75                  80

Val Pro Arg His Leu Phe Ala Glu Lys Tyr Asp Lys Ile Met Leu Asp
                85                  90                  95

Gly Arg Ala Met Thr Asp
            100
```